(12) United States Patent
Holman et al.

(10) Patent No.: US 11,969,568 B2
(45) Date of Patent: Apr. 30, 2024

(54) URETERAL STENT

(71) Applicant: Gyrus ACMI, Inc., Southborough, MA (US)

(72) Inventors: Thomas Holman, Princeton, MN (US); Hui Tang, Acton, MA (US); Judy Walish, West Roxbury, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 832 days.

(21) Appl. No.: 16/929,672

(22) Filed: Jul. 15, 2020

(65) Prior Publication Data

US 2020/0345990 A1 Nov. 5, 2020

Related U.S. Application Data (63) Continuation of application No. 15/662,973, filed on Jul. 28, 2017, now Pat. No. 10,881,842.

(51) Int. Cl.
*A61M 27/00* (2006.01)
*A61M 25/04* (2006.01)
*A61M 25/02* (2006.01)
*A61M 39/24* (2006.01)

(52) U.S. Cl.
CPC .......... *A61M 27/008* (2013.01); *A61M 25/04* (2013.01); *A61M 27/006* (2013.01); *A61M 2025/0233* (2013.01); *A61M 39/24* (2013.01)

(58) Field of Classification Search
CPC . A61F 2/82; A61F 2002/821; A61M 25/0021; A61M 25/003; A61M 25/0075; A61M 25/04; A61M 27/006; A61M 27/008; A61M 39/24; A61M 2025/0076; A61M 2025/0078; A61M 2025/0233; A61M 2202/0496

See application file for complete search history.

(56) References Cited

U.S. PATENT DOCUMENTS

| | | | |
|---|---|---|---|
| 4,738,667 A | 4/1988 | Galloway | |
| 9,186,480 B2 | 11/2015 | Olsen | |
| 10,881,842 B2 | 1/2021 | Holman et al. | |
| 2003/0109930 A1* | 6/2003 | Bluni | A61F 2/04 623/23.7 |
| 2003/0120261 A1 | 6/2003 | Gellman | |

(Continued)

FOREIGN PATENT DOCUMENTS

| | | |
|---|---|---|
| CA | 2875985 A1 | 12/2013 |
| CN | 201759704 U | 3/2011 |

(Continued)

OTHER PUBLICATIONS

"Chinese Application Serial No. 201810627898.3, Office Action dated Sep. 3, 2021", w/ English Translation, 16 pgs.

(Continued)

*Primary Examiner* — Benjamin J Klein (74) *Attorney, Agent, or Firm* — Schwegman Lundberg & Woessner, P.A.

(57) ABSTRACT

Disclosed herein is ureteral stent. The ureteral stent includes a proximal end, a distal end, and a middle portion. The proximal end includes a retention feature having a coiled shape. The distal end is opposite the proximal end. The middle portion is between the proximal end and the distal end.

16 Claims, 12 Drawing Sheets

(56) References Cited

U.S. PATENT DOCUMENTS

| | | | |
|---|---|---|---|
| 2003/0181842 A1* | 9/2003 | Gellman | A61M 27/008 623/1.36 |
| 2004/0059279 A1 | 3/2004 | Mcweeney et al. | |
| 2009/0024091 A1* | 1/2009 | Li | A61J 15/0038 604/175 |
| 2009/0210045 A1 | 8/2009 | Soerensen et al. | |
| 2012/0136319 A1 | 5/2012 | Triel | |
| 2013/0158675 A1 | 6/2013 | Hutchins, III et al. | |
| 2015/0142127 A1 | 5/2015 | Ponsky et al. | |
| 2016/0038273 A1 | 2/2016 | Eiser | |
| 2016/0199170 A1 | 7/2016 | Biltz | |
| 2017/0021128 A1 | 1/2017 | Erbey, II | |
| 2019/0030303 A1 | 1/2019 | Holman et al. | |
| 2019/0298894 A1 | 10/2019 | Friedrich | |

FOREIGN PATENT DOCUMENTS

| | | |
|---|---|---|
| CN | 102802713 A | 11/2012 |
| CN | 203749985 U | 8/2014 |
| CN | 204158869 U | 2/2015 |
| CN | 204208159 U | 3/2015 |
| CN | 204521068 U | 8/2015 |
| CN | 106137478 A | 11/2016 |
| CN | 109303627 A | 2/2019 |
| CN | 109303627 B | 1/2023 |
| CN | 116035786 A | 5/2023 |
| DE | 202006017068 U1 | 8/2007 |
| EP | 2858710 A1 | 4/2015 |
| EP | 3045201 A1 | 7/2016 |
| EP | 3434308 A1 | 1/2019 |
| EP | 3434308 B1 | 10/2021 |
| JP | 2005312894 A | 11/2005 |
| JP | 2019025315 A | 2/2019 |
| WO | WO-2005102217 A1 | 11/2005 |
| WO | WO-2012019155 A1 | 2/2012 |
| WO | WO-2013185128 A1 | 12/2013 |
| WO | WO-2014159848 A1 | 10/2014 |

OTHER PUBLICATIONS

"U.S. Appl. No. 15/662,973, Advisory Action dated May 21, 2020", 2 pgs.
"U.S. Appl. No. 15/662,973, Final Office Action dated Feb. 21, 2020", 15 pgs.
"U.S. Appl. No. 15/662,973, Non Final Office Action dated Sep. 4, 2019", 9 pgs.
"U.S. Appl. No. 15/662,973, Notice of Allowance dated Jun. 11, 2020", 9 pgs.
"U.S. Appl. No. 15/662,973, Notice of Allowance dated Sep. 4, 2020", 9 pgs.
"U.S. Appl. No. 15/662,973, Response filed May 12, 2020 to Final Office Action dated Feb. 21, 2020", 12 pgs.
"U.S. Appl. No. 15/662,973, Response filed Nov. 15, 2019 to Non Final Office Action dated Sep. 4, 2019", 12 pgs.
"European Application Serial No. 18181191.0, Communication Pursuant to Article 94(3) EPC dated Apr. 20, 2020", 5 pgs.
"European Application Serial No. 18181191.0, Extended European Search Report dated Jan. 3, 2019", 10 pgs.
"European Application Serial No. 18181191.0, Response filed Mar. 23, 2019 to Extended European Search Report dated Jan. 3, 2019", 32 pgs.
"European Application Serial No. 18181191.0, Response filed Oct. 8, 2020 to Communication Pursuant to Article 94(3) EPC dated Apr. 20, 2020", 33 pgs.
"U.S. Appl. No. 15/662,973, Corrected Notice of Allowability dated Nov. 5, 2020", 2 pgs.
"Chinese Application Serial No. 201810627898.3, Office Action dated Apr. 19, 2022", w/ English Translation, 10 pgs.
"Chinese Application Serial No. 201810627898.3, Response filed Jul. 4, 2022 to Office Action dated Apr. 19, 2022", with English claims, 12 pgs.
"Chinese Application Serial No. 201810627898.3, Response Filed Jan. 12, 2022 to Office Action dated Sep. 3, 2021", W/ English Claims, 12 pgs.
"European Application Serial No. 21200605.0, Extended European Search Report dated Feb. 17, 2022", 9 pgs.
"Japanese Application Serial No. 2018-125832, Notification of Reasons for Refusal dated Jun. 6, 2022", w/ English translation, 12 pgs.
U.S. Appl. No. 15/662,973, filed Jul. 28, 2017, Ureteral Stent.
"European Application Serial No. 21200605.0, Response filed Sep. 20, 2022 to Extended European Search Report mailed Feb. 17, 2022", 7 pgs.
"Japanese Application Serial No. 2018-125832, Final Notification of Reasons for Rejection mailed Jan. 10, 2023", w/English Translation, 6 pgs.
"Japanese Application Serial No. 2018-125832, Final Notification of Reasons for Rejection mailed Jul. 31, 2023", W/English Translation, 10 pgs.
"Japanese Application Serial No. 2018-125832, Response filed Mar. 28, 2023 to Final Notification of Reasons for Rejection mailed Jan. 10, 2023", w/ English Claims, 7 pgs.
"Japanese Application Serial No. 2018-125832, Response filed Sep. 6, 2022 to Notification of Reasons for Refusal mailed Jun. 6, 2022", w/ English Claims, 8 pgs.
"Japanese Application Serial No. 2018-125832, Response filed Sep. 20, 2023 to Final Notification of Reasons for Rejection mailed Jul. 31, 2023", w/ english claims, 7 pgs.

* cited by examiner

URETERAL STENT

CROSS REFERENCE TO RELATED APPLICATION

This is a continuation of copending U.S. application Ser. No. 15/662,973 filed Jul. 28, 2017 which is hereby incorporated by reference in its entirety.

BACKGROUND

Field of the Invention

The invention relates to a ureteral stent and more specifically relates to a comfort ureteral stent.

Brief Description of Prior Developments

A ureter is a tubular passageway in the body that conveys urine from a kidney to a bladder. Ureteral stents are used to facilitate urinary drainage from the kidney to the bladder in patients having a ureteral obstruction or injury, or to protect the integrity of the ureter in a variety of surgical manipulations. Ureteral stents are typically about 30 cm long, hollow catheter-like devices made from a polymer and placed within the ureter with a distal end residing in the kidney and a proximal end residing in the bladder.

Accordingly, there is a need to provide improved and reliable ureteral stent configurations that are configured for increased patient comfort.

SUMMARY

In accordance with one aspect of the invention, a ureteral stent is disclosed. The ureteral stent includes a proximal end, a distal end, and a middle portion. The proximal end includes a retention feature having a coiled shape. The distal end is opposite the proximal end. The middle portion is between the proximal end and the distal end.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
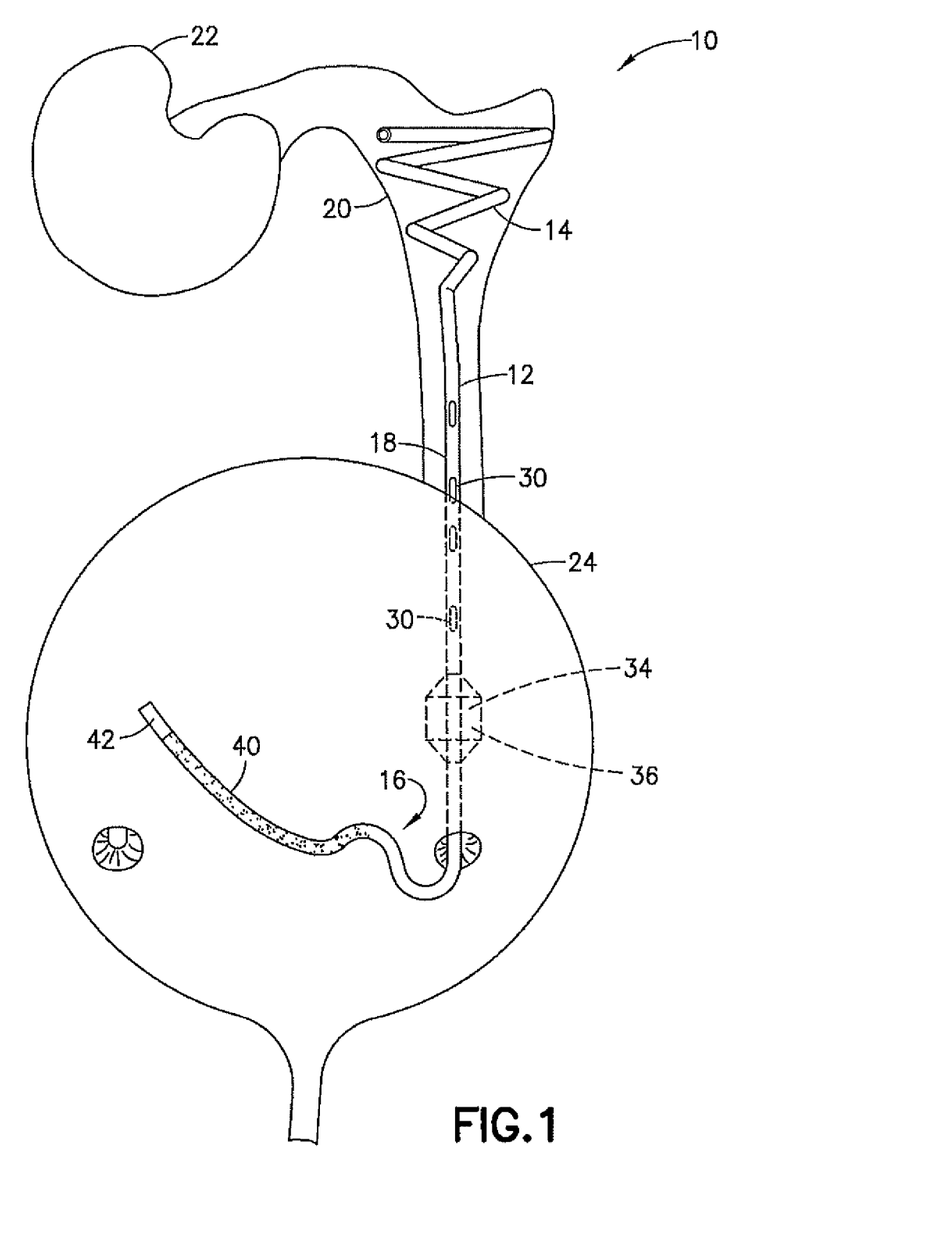
FIG. 1 is a partial perspective view of ureteral stent (within the body of a patient) incorporating features of the invention.

Referring to FIG. 1, there is shown a partial perspective view of a ureteral stent 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

The ureteral stent 10 comprises a tubular member 12 having a proximal end 14, an opposite distal end 16, and a middle portion 18 between the proximal end and the distal end 16. The proximal end 14 is configured to be placed within the renal pelvis 20 of the kidney 22. The distal end 16 is configured to be placed within the bladder 24.

Figure 2:
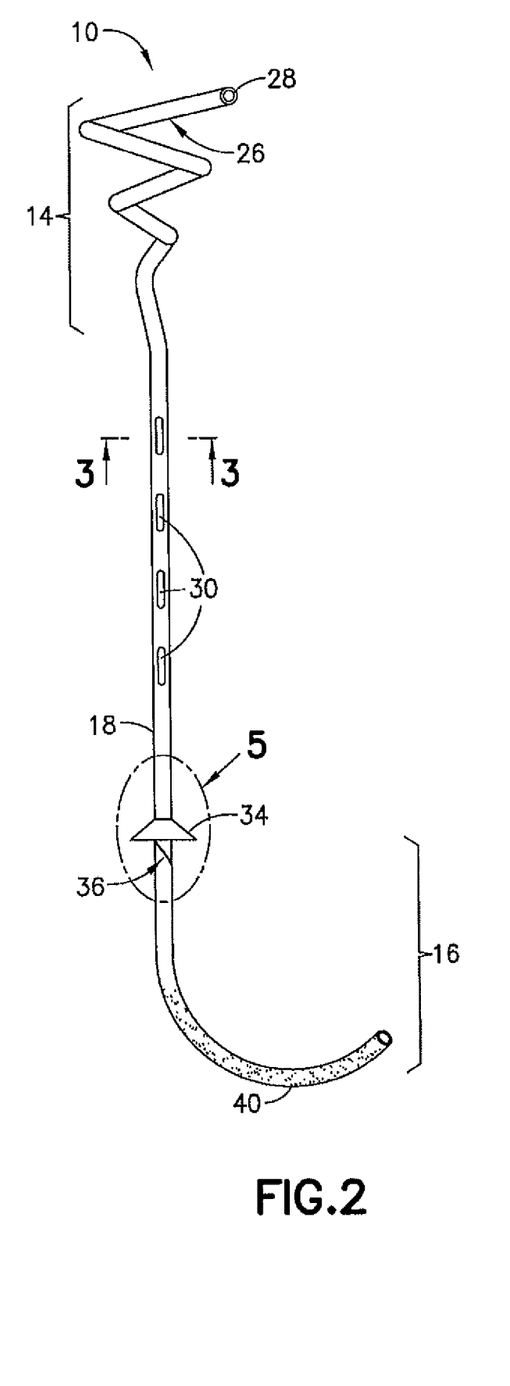
FIG. 2 is another perspective view of the ureteral stent shown in FIG. 1.

Referring now also to FIG. 2, the proximal end 14 comprises a coiled configuration (or shape) having a conical spiral shape 26. The conical spiral shape 26 extends away from the middle portion 18 such that the diameter of the conical spiral shape 26 increases as the shape extends away from the middle portion and a first open end 28 of the stent 10 is at substantially the largest diameter portion of the conical spiral shape 26.

The conical spiral shape 26 of the proximal end 14 is configured to allow for anchoring of the proximal end 14 within the renal pelvis. This provides a retention mechanism which reduces the contact force placed on the pelvis wall (of the renal pelvis 20) by providing increased surface area of contact between the proximal end and the pelvis wall when compared to conventional configurations.

Figure 3:
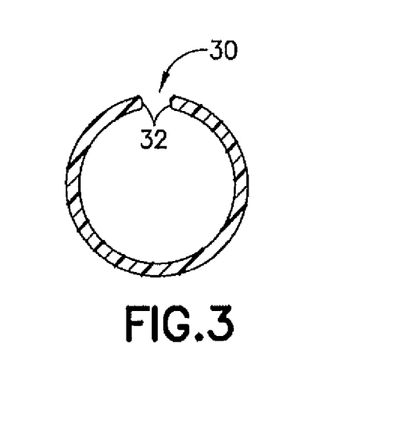
FIG. 3 is a section view of the indicated section line in FIG. 2.

The middle portion 18 comprises side holes (or openings) 30 extending through a wall of the tubular member. Referring now also to section view 3-3, the side holes 30 are configured to have smooth edges (or smooth opening surfaces) 32. The smooth edges may be provided by any suitable machining or fabrication operation capable of rounding the edges (such as by providing a fillet, blend, corner radius, or rounded corner, at the edges 32). According to various exemplary embodiments, the smoothing process may include a punch process wherein during the punching the polymer is melted removing any sharp edges. Also, the edges can be post operatively melted with a hot air, flame or hot tool, for example. The smooth edges may be provided any suitable edge areas of the holes 32 between an inside diameter and an outside diameter of the tubular member.

It should be noted that although various figures illustrate the stent 10 as comprising four side holes 30 at the middle portion 18, one skilled in the art will appreciate that the various exemplary embodiments are not necessarily so limited and that alternate embodiments may comprise any suitable number of side holes. For example in some embodiments, the stent may comprise one or more side holes, in other embodiments the stent may comprise five or more side holes, and it should be understood that any number of side holes may be provided. Additionally, the side holes 30 may be provided at any one, or combination of, the proximal end 14, the distal end 16, and/or the middle portion 18 (with any suitable number of side holes at each end 14, 16 or the middle portion 18), including at retention portions or other shaped features of the ends.

As the urethra elongates and contracts with bladder voiding action, this movement results in the ureter rubbing against the edges 32 of the holes 30. This "smooth" hole configuration is configured to reduce irritation and patient pain. In addition to the smooth aspect of the hole edge configuration for patient comfort, the smooth edges are also provided to reduce turbulence of urine flow (as it promotes encrustation). This smooth edge configuration of the holes reduces turbulence during flow down the ureter whether it is gravity feed or the peristaltic action of the ureter itself. Additionally, the position of the holes may play a role in urine reflux (discussed further below).

Figure 4:
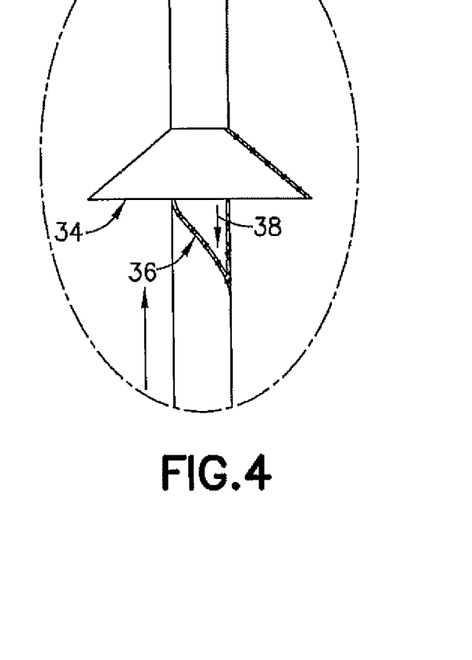
FIG. 4 is an enlarged view of the indicated portion in FIG. 2.

According to various exemplary embodiments, the stent 10 may further comprise an exterior reflux skirt 34 and/or an interior reflux valve 36 between the middle portion 18 and the distal end 16. The exterior reflux skirt 34 surrounds a portion of the tubular member with a general cone shape and is configured to minimize exterior reflux flow. The interior reflux valve 36 is configured to provide one way flow through the tubular member (see arrow 38). According to various exemplary embodiments, the interior reflux valve 36 may be a duck bill valve, however in alternate embodiments, any suitable type of valve allowing for one way flow may be provided, such as a check valve, for example.

The distal end 16 comprises a tail portion (or tip portion) 40 configured to be received within the bladder proximate a zone or region called the "Trigon". The Trigon has copious nerve endings signaling the need to void the bladder and when voiding is complete. Contact with the trigon zone causes much of the patient's discomfort. The tail portion 40 comprises a foam material and is configured such that the tail portion "floats" in water/urine in the bladder (with the foam having a specific gravity <1.0, for example) minimizing (or eliminating) contact with the trigon when any urine is present. Although the tail portion is described above as having a foam material, one skilled in the art will appreciate the exemplary embodiments are not necessarily so limited, and that alternate embodiments may comprise any suitable material configured to float in the bladder, such as configurations having "trapped" air in the side walls to achieve floating, for example.

Figure 5:
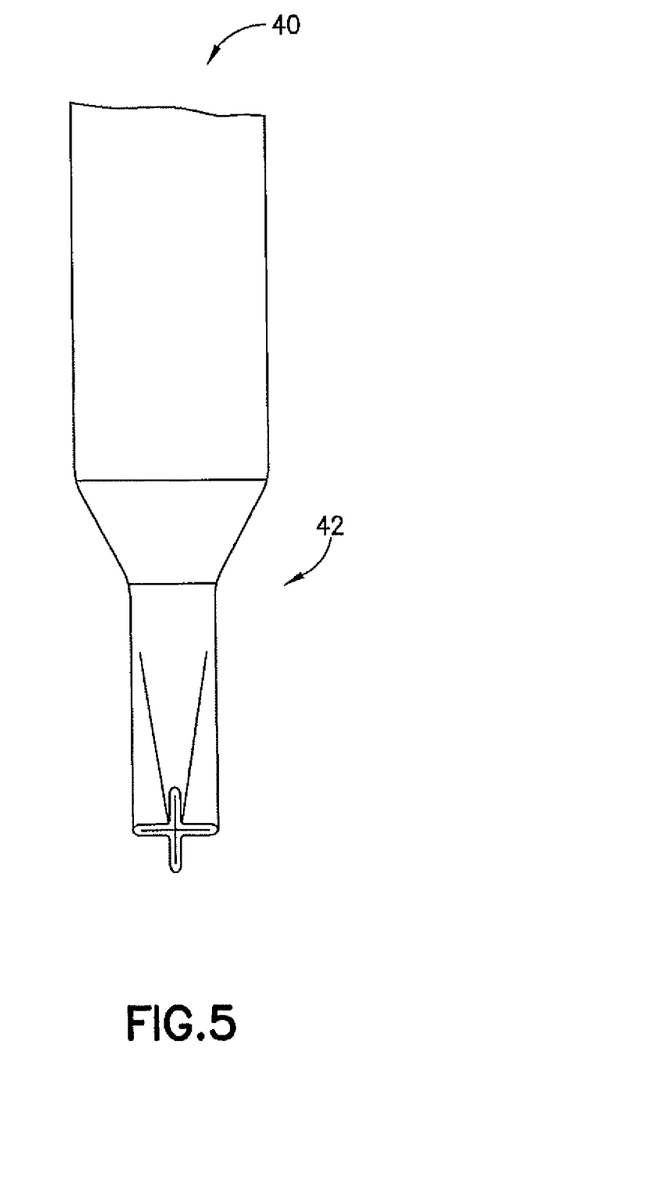
FIG. 5 is a partial view of a tail portion of the ureteral stent shown in FIG. 1.

According to various exemplary embodiments, the tail portion 40 may further comprise a one-way urine flow valve 42 enabling reductions in urine reflux (urine flow back up the ureter to the kidney). The configuration of the distal tail 40 including the one-way valve 42 requires no additional components as it comprises a folded tube heat set feature as shown in FIG. 5. According to various exemplary embodiments, the configuration of the one-way urine flow valve 42 may be similar to the configuration of a duck bill valve, however a duck valve may generally be wider than the normal tubular outside diameter (OD) and a 4-wing valve could be smaller than the OD. Multiple wing configurations may also apply in some embodiments. In situ, the one-way valve 42 substantially eliminates reflux through the stent lumen but not exterior to the stent.

Figures 6, 7:
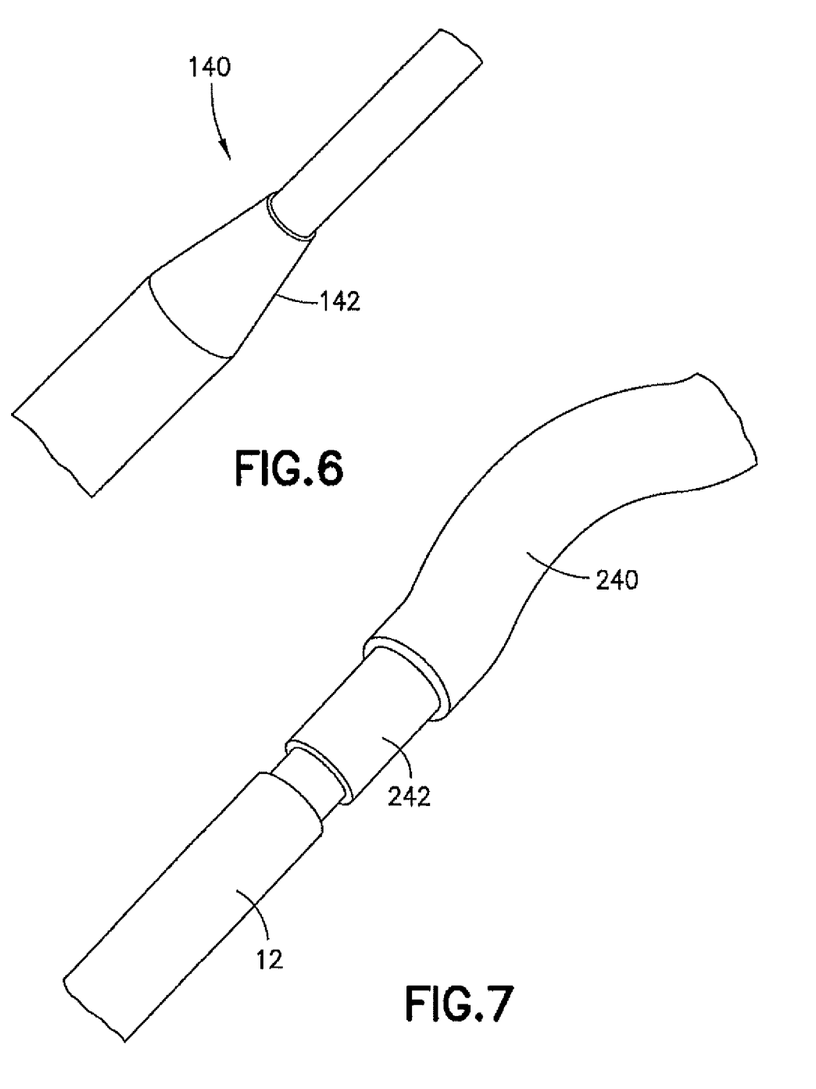
FIGS. 6 and 7 are perspective views of alternate configurations of a floating tip portion of the ureteral stent shown in FIG. 1.

FIGS. 6 and 7 illustrate alternate configurations of the floating tip portion. The floating tip portion 140 is similar to the tip portion 40, however in this embodiment the tip portion 140 comprises a tapered portion 142. Additionally, the floating tip portion 240 is similar to the tip portion 40 and comprises a reflux valve 242 which is fitted within an end portion of the tubular member 12.

According to the various exemplary embodiments, an exterior anti-reflux feature 34, 36 may be provided to substantially eliminate the urine flow around the exterior of the stent. The combination of the distal valve 42 within the bladder and exterior valve 36 near the midpoint of the stent and providing holes 30 having smooth low turbulence side edges 32 above or on the kidney side of the exterior reflux feature provides for reduction of urine reflux. Additionally, in some embodiments the distal end 16 may comprise a J-hook migration lock 44 configured to prevent migration of the stent due to patient movement.

Figures 8, 9:
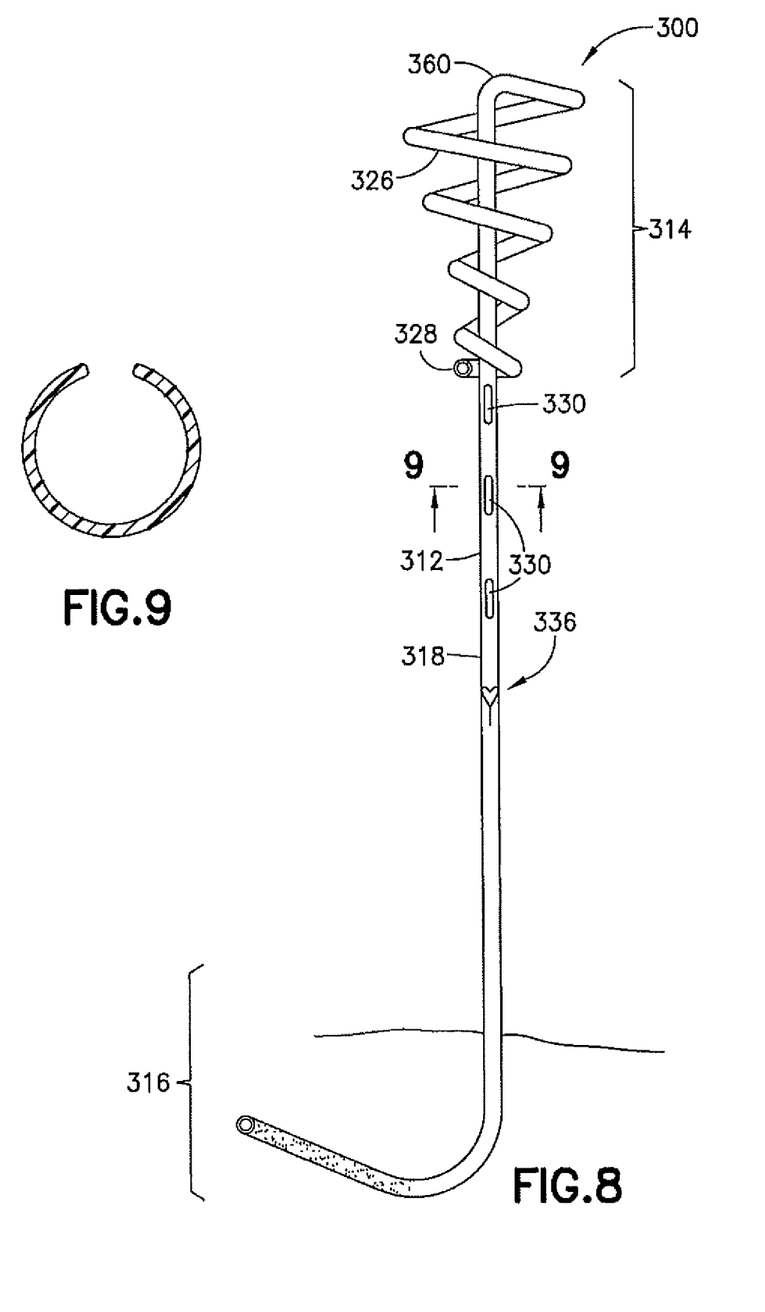
FIG. 8 is a perspective view of another example ureteral stent incorporating features of the invention.
FIG. 9 is a section view of the indicated section line in FIG. 8.

Referring now also to FIG. 8 another embodiment of the stent is shown. In this embodiment, the stent 300 comprises a distal end 316 similar to the distal end 16 shown in FIGS. 1, 2, and middle portion 318 similar to the middle portion 18 shown in FIGS. 1, 2 (with holes 330 similar to holes 30 and valve 336 similar to valve 36). However, at the proximal end 314 the tubular member 312 comprises a bend portion 360 which extends to the largest diameter portion of the spiral conical shape 326. The conical spiral shape 326 surrounds the tubular member 312 and extends towards the middle portion 318 such that the diameter of the conical spiral shape 326 decreases as the shape extends towards the middle portion 318 and a first open end 328 of the stent 300 is at substantially the smallest diameter portion of the conical spiral shape 326. In this embodiment, the conical spiral shape 326 is configured to lock the distal end into position, and the top portion of the conical spiral shape (i.e. largest diameter portion) allows a spring action as ureteral contracts.

Figure 10:
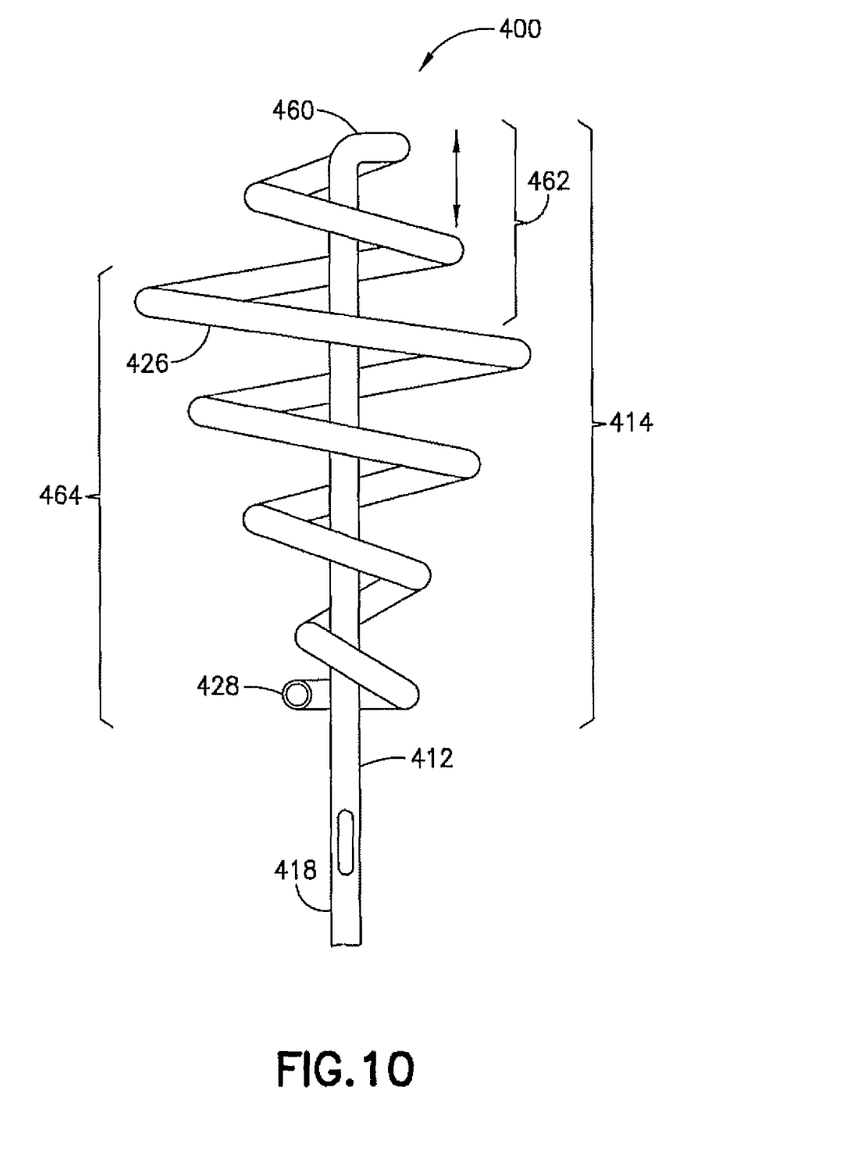
FIG. 10 is an alternate embodiment of the proximal end shown in FIG. 8.

Referring now also to FIG. 10, another alternate embodiment of the proximal end is shown. The proximal end 414 comprises a dual conical spiral shape 426 having a spring region 462 and an anchor region 464. Similar to the configuration shown in FIG. 8, the tubular member 412 comprises a bend portion 460. However from the bend portion, the spring region 462 of the conical spiral shape increases in a direction away from the bend portion and the largest diameter portion of the spiral conical shape 426 is between the spring region 462 and the anchor region 464. The conical spiral shape 426 surrounds the tubular member 412 and extends towards the middle portion 418 such that the diameter of the conical spiral shape 426 decreases as the shape extends from the spring region towards the middle portion 318 and a first open end 428 of the stent 400 is at substantially the smallest diameter portion of the conical spiral shape 426.

Figure 11:
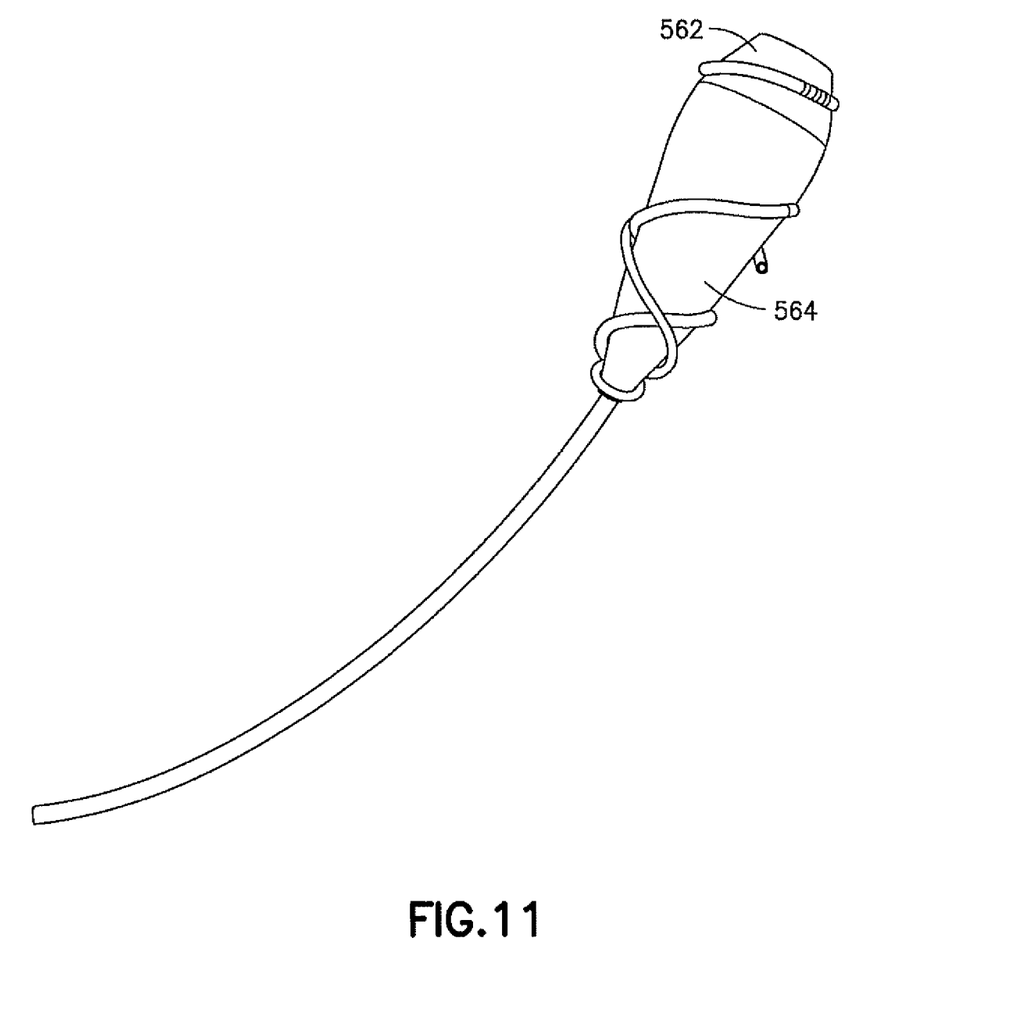
FIG. 11 is a perspective view showing a fixture corresponding to the proximal end shown in FIG. 10.

According to various exemplary embodiments the dual conical spring shape may be provided with a heat set fixture comprising two conical regions 562, 564 which correspond to the regions 462, 464, of the conical spiral shape 426 (see FIG. 11). However, it should be noted that the fixture shown in FIG. 11 is merely exemplary and any suitable type of fixture may be provided.

Figure 12:
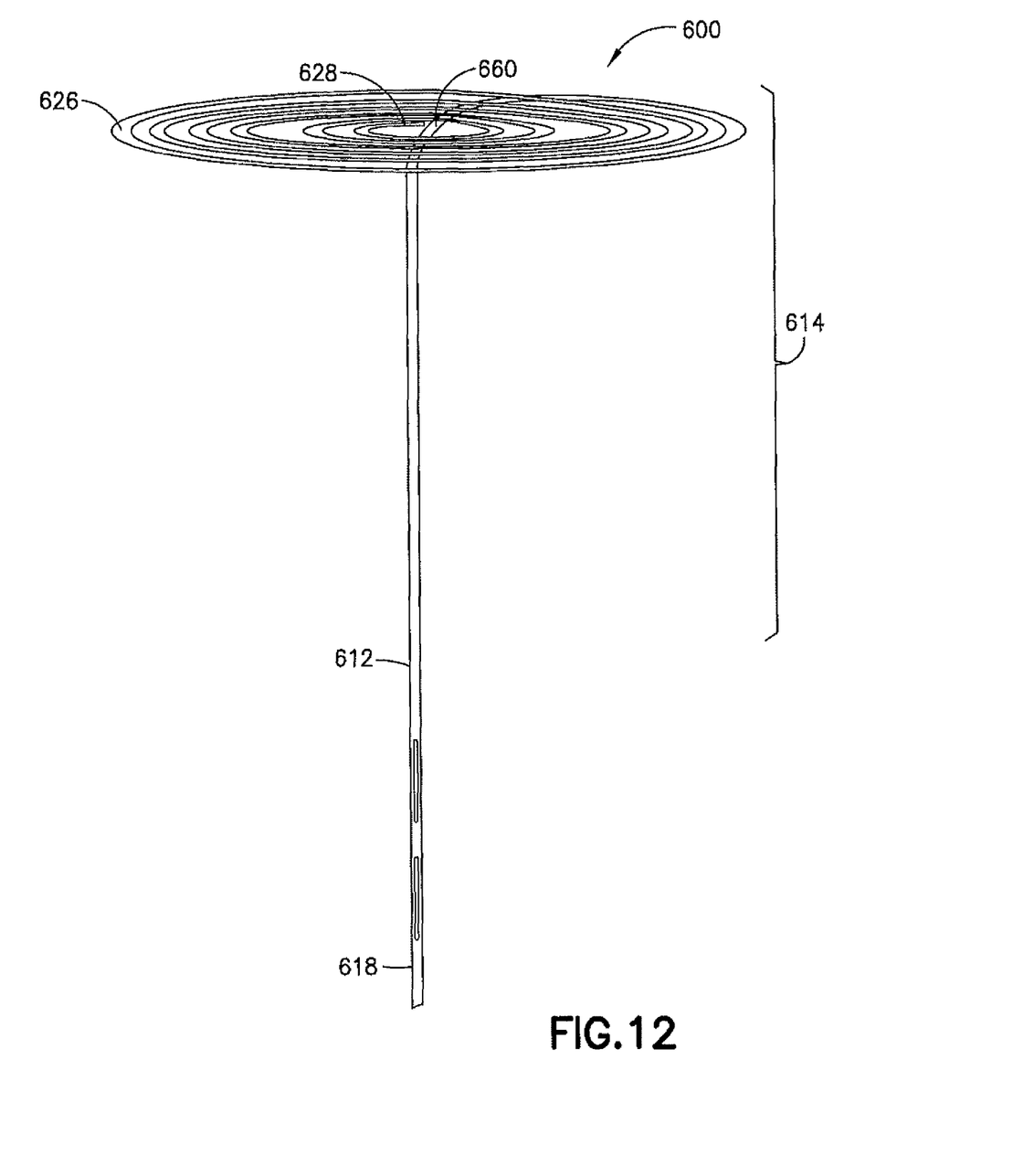
FIG. 12 is another alternate embodiment of the proximal end shown in FIG. 8.

Referring now also to FIG. 12, another alternate embodiment of the proximal end is shown. Similar to the proximal end shown in FIG. 8, the proximal end 614 comprises a bend portion 660 and a first open end 628. However in this embodiment, the proximal end 614 comprises a coiled shape 626 which lies substantially in a plane orthogonal to the middle portion 618 of the stent 600. The coiled shape 626 surrounds the end of the tubular member 612 in a coiled/spiraled fashion.

Figure 13:
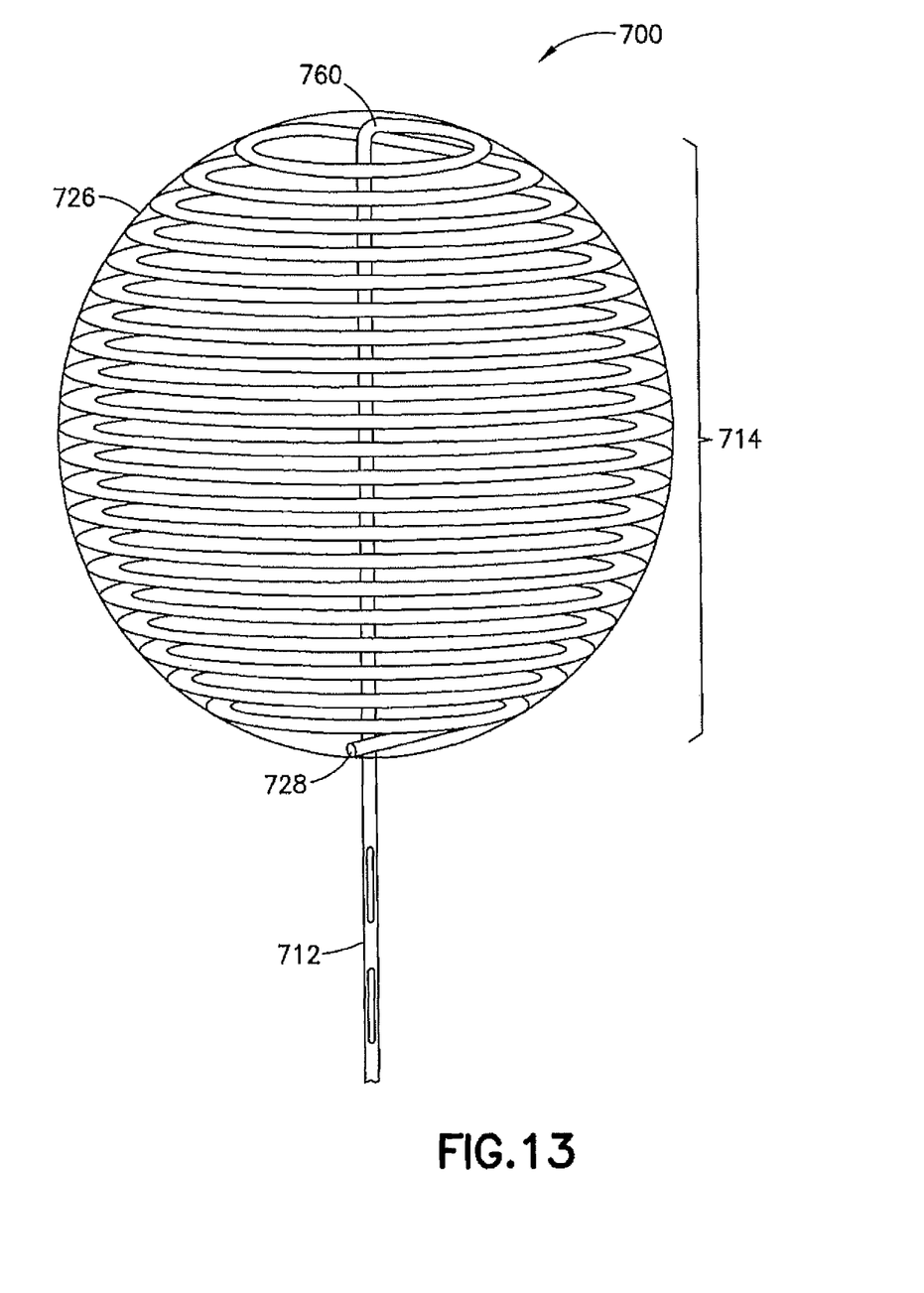
FIG. 13 is another alternate embodiment of the proximal end shown in FIG. 8.

Referring now also to FIG. 13, another alternate embodiment of the proximal end is shown. Similar to the proximal end shown in FIG. 8, the proximal end 714 comprises a bend portion 760 and a first open end 728. However in this embodiment, the proximal end 714 comprises a coiled section having a general spherical or bulb-like shape 726. The coiled spherical or bulb-like shape 726 surrounds a portion at the end of the tubular member 712 of the stent 700.

Figures 14, 15, 16:
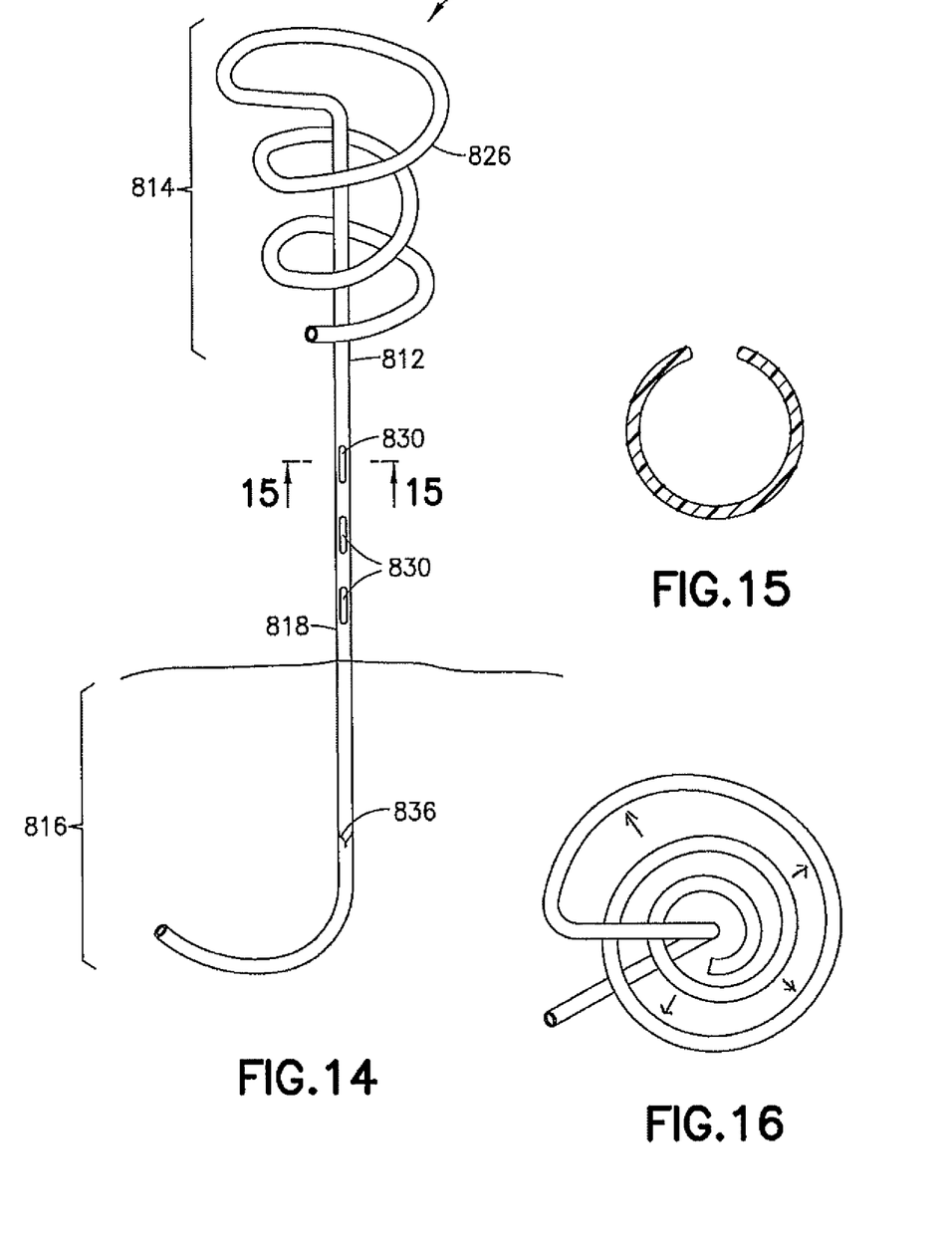
FIG. 14 is a perspective view of another example ureteral stent incorporating features of the invention.
FIG. 15 is a section view of the indicated section line in FIG. 14.
FIG. 16 is a top view of the ureteral stent shown in FIG. 14.
Figure 17:
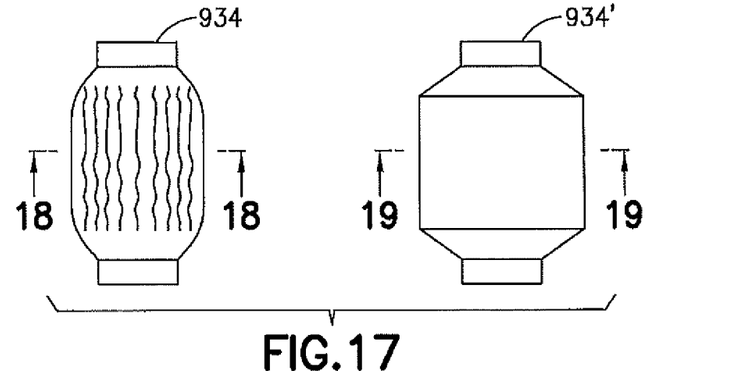
FIGS. 17-20 are alternate exterior valve configurations according to various embodiments of the ureteral stent.
Figures 18, 19, 20:
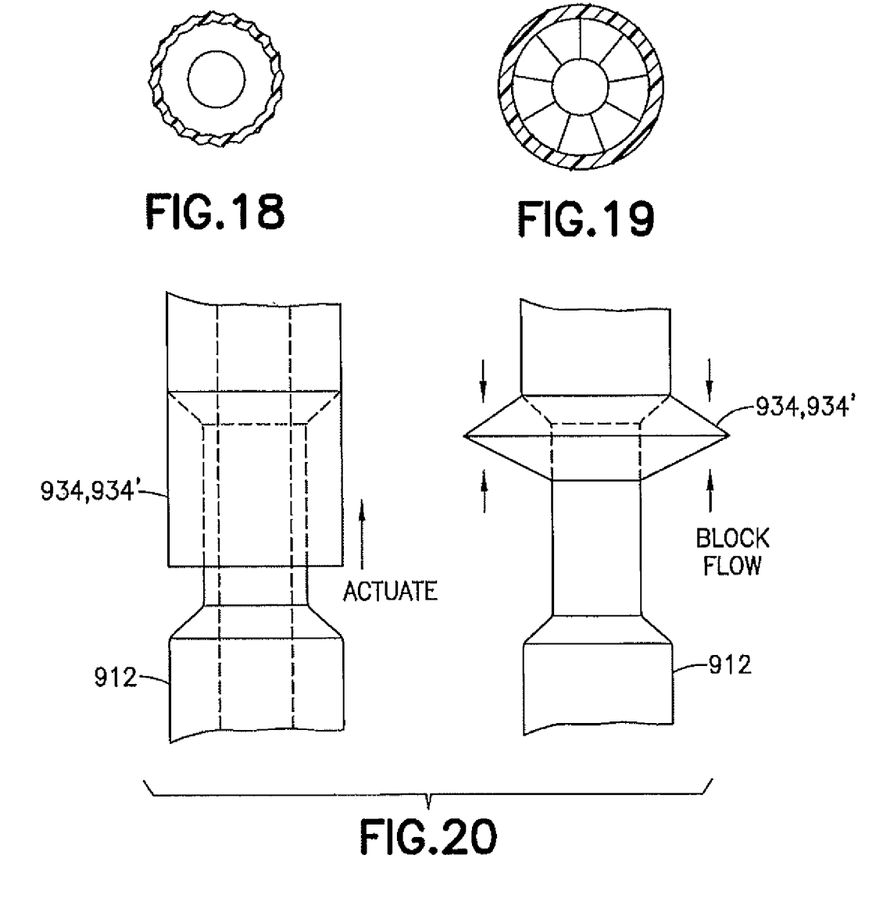

Referring now also to FIG. 14 another embodiment of the stent is shown. In this embodiment, the stent 800 comprises a distal end 816 similar to the distal end 316 shown in FIG. 8, and middle portion 818 similar to the middle portion 318 shown in FIG. 8 (with holes 830 similar to holes 330 and valve 836 similar to valve 336). However, at the proximal end 814 the spiral conical shape 826 comprises a reverse spiral (see FIG. 16) compared to the configuration shown in FIG. 8 (in other words, when viewed from the top, the spiral has a 'clockwise' configuration from largest diameter to smallest diameter, whereas the configuration in FIG. 8 when viewed from the top, the spiral has a 'counter-clockwise' configuration from largest diameter to smallest diameter). Additionally, FIG. 16 illustrates (see arrows) where holes 830 are also provided on the internal surface (i.e. surface facing the tubular member 812) of the conical spiral shape 826. However, it should be noted that the holes 830 may be provided at any suitable surface portion of the conical spiral shape 826.

FIGS. 17-20 illustrate various exemplary embodiments of the exterior reflux skirt 34 (shown in FIG. 4), however the reflux skirt (or valve) 934, 934', are configured to actuate, and in some embodiments shorten, over a narrowed portion of the tubular member 912. As the exterior valve 934, 934' shortens, it expands radially creating a larger portion of the stent to therefore block exterior liquid flow.

Figure 21:
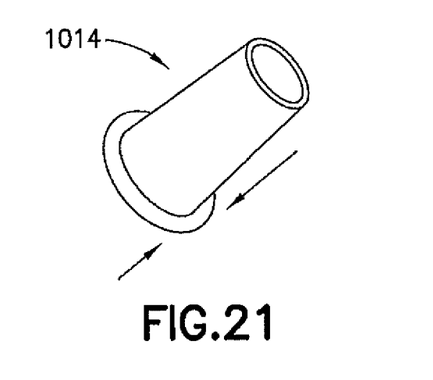
FIGS. 21, 22 are alternate proximal portion configurations according to various embodiments of the ureteral stent.
Figure 22:
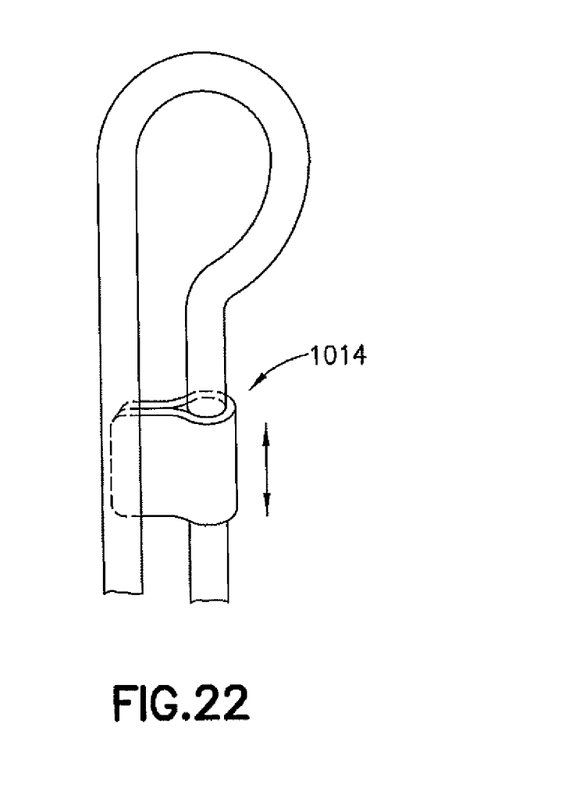

FIGS. 21, 22 illustrate an exemplary embodiment of a proximal portion 1014 that is configured to be adjustable to fit within the renal pelvis of various patients. However, it should be noted that the adjustable portions illustrated in FIGS. 21, 22 may comprise any suitable configuration.

Technical effects of any one or more of the exemplary embodiments provide significant advantages over conventional configurations having side holes which are typically punched or drilled through the wall resulting in a sharp edge(s). The exemplary embodiments disclosed herein provide a smooth hole edge configuration (providing smooth exterior ports) which reduces patient pain and provides greater comfort.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a ureteral stent comprising: a proximal end comprising a retention feature having a coiled shape; a distal end opposite the proximal end; and a middle portion between the proximal end and the distal end.

A ureteral stent as above, wherein the middle portion comprises at least one opening having smooth opening surfaces.

A ureteral stent as above, wherein the at least one opening comprises rounded edges.

A ureteral stent as above, wherein the coiled shape is a spiral shape.

A ureteral stent as above, wherein the retention feature has a conical coiled shape.

A ureteral stent as above, wherein the coiled shape retention feature lies substantially on a plane orthogonal to the plane the middle portion lies on.

A ureteral stent as above, wherein the retention feature comprises a general spherical shape.

A ureteral stent as above, wherein the distal end comprises a tail portion configured to float.

A ureteral stent as above, wherein the retention feature comprises a dual conical spiral shape.

A ureteral stent as above, further comprising a one-way valve between the middle portion and the distal end.

A ureteral stent as above, further comprising a one-way valve at the distal end.

A ureteral stent as above, wherein the distal end comprises a retention feature.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A ureteral stent comprising:
    a proximal end comprising a retention feature having a coiled portion;
    a distal end opposite the proximal end; and
    a middle portion between the proximal end and the distal end,
    wherein the retention feature comprises a substantially spherical periphery shape surrounding a portion of the middle portion, and
    where the proximal end is configured to be located in a kidney of a patient, where a distal end of the substantially spherical periphery shape has a fluid entrance aperture into the coiled portion, and wherein the coiled portion forms a substantially closed tube between the fluid entrance aperture and the middle portion.

2. The ureteral stent as claimed in claim 1 where the substantially spherical periphery shape comprises a bulb-like shape.

3. The ureteral stent as claimed in claim 1 where the proximal end comprised at least one additional fluid entrance aperture into the coiled portion.

4. The ureteral stent as claimed in claim 1 where the coiled portion extends towards the middle portion from an end of the middle portion.

5. The ureteral stent as claimed in claim 4 where the coiled portion comprises a fluid entrance aperture into the coiled portion at a distal end of the coiled portion proximate the middle portion.

6. The ureteral stent as claimed in claim 1 where the distal end comprises a tail portion configured to float.

7. The ureteral stent as claimed in claim 6 where the tail portion comprises a foam material.

8. The ureteral stent as claimed in claim 6 where the tail portion comprises a trapped gas in a side wall of the tail portion.

9. A ureteral stent comprising:
   a first end comprising a retention feature, wherein the retention feature comprises a coiled portion forming a substantially spherical periphery shape, the coiled portion having a fluid entrance aperture into the coiled portion at a distal end of the coiled portion, wherein the first end is configured to be located in a kidney of a patient;
   a second end opposite the first end; and
   a middle portion between the first end and the second end, the middle portion comprising a conduit for flow of fluid from the first end to the second end,
   wherein the coiled portion extends towards the middle portion from the first end,
   where the first end is configured to be located in a kidney of a patient, where a distal end of the substantially spherical periphery shape has a fluid entrance aperture into the coiled portion, and wherein the coiled portion forms a substantially closed tube between the fluid entrance aperture and the middle portion.

10. The ureteral stent as claimed in claim 9 where the substantially spherical periphery shape comprises a bulb-like shape.

11. The ureteral stent as claimed in claim 9 where the substantially spherical periphery shape surrounds a portion of the middle portion.

12. The ureteral stent as claimed in claim 9 where a distal end of the substantially spherical periphery shape has a fluid entrance aperture into the coiled portion, and where the coiled portion forms a substantially closed tube between the fluid entrance aperture and the middle portion.

13. The ureteral stent as claimed in claim 12 where the first end comprised at least one additional fluid entrance aperture into the coiled portion.

14. The ureteral stent as claimed in claim 9 where the second end comprises a tail portion configured to float.

15. The ureteral stent as claimed in claim 14 where the tail portion comprises at least one of a foam material or trapped gas in a side wall of the tail portion.

16. A ureteral stent comprising:
   a proximal end comprising a retention feature, where the retention feature comprises a substantially spherical periphery shape, where the proximal end is configured to be located in a kidney of a patient;
   a distal end opposite the proximal end; and
   a middle portion between the proximal end and the distal end, where the middle portion comprised a conduit for flow of fluid from the proximal end at the kidney to the distal end,
   where the substantially spherical periphery shape extends towards the middle portion, wherein the substantially spherical periphery shape comprises a fluid entrance aperture into the substantially spherical periphery shape at a distal end of the substantially spherical periphery shape, and where the fluid entrance aperture is located proximate the middle portion,
   where the proximal end is configured to be located in a kidney of a patient, where a distal end of the substantially spherical periphery shape has a fluid entrance aperture into a coiled portion, and wherein the coiled portion forms a substantially closed tube between the fluid entrance aperture and the middle portion.

* * * * *